United States Patent
Lee (10) Patent No.: US 12,150,962 B2
(45) Date of Patent: Nov. 26, 2024

(54) METHOD FOR PRODUCING EXTRACELLULAR VESICLES COMPRISING FETUS-DERIVED PRIMAL IMMUNOGLOBULIN

(71) Applicant: STEMMEDICARE CO., LTD., Seoul (KR)

(72) Inventor: Jang Ho Lee, Seoul (KR)

(73) Assignee: STEMMEDICARE CO., LTD., Seoul (KR)

( * ) Notice: Subject to any disclaimer, the term of this patent is extended or adjusted under 35 U.S.C. 154(b) by 0 days.

(21) Appl. No.: 17/923,871

(22) PCT Filed: Jul. 16, 2021

(86) PCT No.: PCT/KR2021/009189
§ 371 (c)(1),
(2) Date: Nov. 7, 2022

(87) PCT Pub. No.: WO2022/154205
PCT Pub. Date: Jul. 21, 2022

(65) Prior Publication Data
US 2023/0165902 A1     Jun. 1, 2023

(30) Foreign Application Priority Data

Jan. 14, 2021   (KR) ........................ 10-2021-0005498

(51) Int. Cl.
*A61K 35/28* (2015.01)
*C07K 14/74* (2006.01)
*C07K 16/00* (2006.01)
*C12N 5/0775* (2010.01)

(52) U.S. Cl.
CPC ........ *A61K 35/28* (2013.01); *C07K 14/70539* (2013.01); *C07K 16/00* (2013.01); *C12N 5/0668* (2013.01); *C12N 2500/02* (2013.01); *C12N 2502/1171* (2013.01); *C12N 2502/137* (2013.01); *C12N 2509/00* (2013.01)

(58) Field of Classification Search
CPC ........ A61K 35/28; A61K 35/50; A61K 35/51; C07K 14/70539; C07K 16/00; C12N 5/0668; C12N 2502/1171; C12N 2502/137; C12N 5/0605; C12N 5/0647
See application file for complete search history.

(56) References Cited

U.S. PATENT DOCUMENTS

| | | | |
|---|---|---|---|
| 2020/0041391 A1 | 2/2020 | Inuzuka et al. | |
| 2021/0147797 A1 | 5/2021 | Lee | |

FOREIGN PATENT DOCUMENTS

| | | | |
|---|---|---|---|
| KR | 10-1980726 B1 | 5/2019 | |
| KR | 10-2252325 B1 | 5/2021 | |
| WO | WO-2018015539 A1 * | 1/2018 | ............. A61K 39/44 |
| WO | 2018-070479 A1 | 4/2018 | |

OTHER PUBLICATIONS

Kim et al. Exosomes derived from human umbilical cord blood mesenchymal stem cells stimulates rejuvenation of human skin. Biochemical and Biophysical Research Communications 493 (2017) 1102-1108 (Year: 2017).*
Mallis et al. Evaluation of HLA-G Expression in Multipotent Mesenchymal Stromal Cells Derived from Vitrified Wharton's Jelly Tissue. Bioengineering, 5, 95: p. 1-16 (Year: 2018).*
Magatti et al. The Immunomodulatory Properties of Amniotic Cells: The Two Sides of the Coin. Cell Transplantation. vol. 27(1) 31-44 (Year: 2018).*
Tracy et al. A comparison of clinically relevant sources of mesenchymal stem cell-derived exosomes: Bone marrow and amniotic fluid. Journal of Pediatric Surgery 54:p. 86-90 (Year: 2019).*
Balbi et al. First Characterization of Human Amniotic Fluid Stem Cell Extracellular Vesicles as a Powerful Paracrine Tool Endowed with Regenerative Potential. Stem Cells Translationalmedicine 2017;6:1340-1355 (Year: 2017).*
Lee et al. The Different Immune Responses by Age Are due to the Ability of the Fetal Immune System to Secrete Primal Immunoglobulins Responding to Unexperienced Antigens. Int. J. Biol. Sci. 2022, vol. 18, p. 1-20 (Year: 2022).*
Admyre et al. "Exosomes with Immune Modulatory Features Are Present in Human Breast Milk" J Immunol 2007; 179:1969-1978; Aug. 1, 2007.
Qiu et al. "Functional proteins of mesenchymal stem cell-derived extracellular vesicles" Qiu et al. Stem Cell Research & Therapy (Mar. 2019).
Cho et al. "Study of immune-tolerized cell lines and extracellular vesicles inductive environment promoting continuous expression and secretion of HLA-G from semiallograft immune tolerance during pregnancy" Journal of Extracellular Vesicles; Jul. 2020, vol. 9, 1795364.
Trapani et al., "Immune Regulatory Properties of CD117pos Amniotic Fluid Stem Cells Vary According to Gestational Age" Stem Cells and Development, vol. 24, No. 1 2015, Jul. 29, 2014.

(Continued)

*Primary Examiner* — Taeyoon Kim
(74) *Attorney, Agent, or Firm* — Maschoff Brennan (57) ABSTRACT

A fetal stem cell-derived extracellular vesicle has immune tolerance properties. The extracellular vesicle containing a fetal stem cell-derived primal immunoglobulin contains various natural antibodies and complement proteins which can immediately respond to foreign infectious agents such as viruses, bacteria, pathogens, etc., and thus can effectively treat and prevent infectious diseases through an enhanced innate immune system. Methods are disclosed for preparing the fetal stem cell-derived extracellular vesicle.

6 Claims, 6 Drawing Sheets

(56) References Cited

OTHER PUBLICATIONS

Loukogeorgakis et al., "Amniotic Fluid Stem Cells: The Known, The Unknown and Potential Regenerative Medicine Applications" Stem Cells, Regenerative Medicine, Oct. 1, 2016.

Ditadi et al., "Human and murine amniotic fluid c-Kit+Lin- cells display hematopoietic activity" Hematopoiesis and Stem Cells, Blood, Apr. 23, 2019, vol. 113, No. 17.

* cited by examiner

METHOD FOR PRODUCING EXTRACELLULAR VESICLES COMPRISING FETUS-DERIVED PRIMAL IMMUNOGLOBULIN

TECHNICAL FIELD

The present invention relates to a fetal stem cell-derived extracellular vesicle with immune tolerance properties, containing immunoglobulin M, immunoglobulin A, immunoglobulin D, immunoglobulin G, immunoglobulin G3 and immunoglobulin E; a method for preparing the fetal stem cell-derived extracellular vesicle with immune tolerance properties under culture conditions similar to those of the body during pregnancy; a pharmaceutical composition including the above-mentioned extracellular vesicle for preventing or treating infectious diseases caused by a foreign infectious agent; and a composition for enhancing innate immunity.

BACKGROUND ART

Immunity refers to a defense mechanism, in which an organism distinguishes itself from non-self and protects itself from externally invading microorganisms such as viruses, bacteria, pathogens, etc., and products abnormally generated in the body, such as cancer, by recognizing them as non-self-antigens, and immunity is largely divided into innate immunity and adaptive (acquired) immunity.

Innate immunity refers to an immune system that responds non-specifically and immediately to non-self-antigens without distinction of specific pathogens, and can be said to be a primary defense system against infection by reacting immediately to invading foreign pathogens and activating adaptive immunity by transmitting information about non-self-antigens. Immune cells involved in innate immunity include phagocytic macrophages, monocytes, dendritic cells, natural killer (NK) cells, granulocytes, innate lymphoid cells, etc., and B1 cells, an early developmental form of B cells known to be mainly involved in adaptive immunity, are also involved in innate immunity. Meanwhile, adaptive immunity refers to an immune system that is activated with a delay for a certain period of time by binding between a non-self-antigen presented by the innate immune system and a specific receptor that recognizes the non-self-antigen, and is divided into cellular immunity by T cells having a T-cell receptor (TCR) and humoral immunity by B cells having a B-cell receptor (BCR).

In particular, B cells become plasma cells through a maturation process and produce antibodies capable of specifically binding to non-self-antigens delivered through the BCR. These antibodies are proteins that bind to a specific antigen and play roles such as activation of complement, opsonic action, neutralization/inactivation of toxins and viruses, and induction of antibody-dependent cytotoxicity, and are also called immunoglobulin. Immunoglobulin consists of two heavy chains and two light chains. It is divided into five types, immunoglobulin M, immunoglobulin G, immunoglobulin A, immunoglobulin D, and immunoglobulin E depending on the type of heavy chains, each of which has a biological defense action in the body.

IgM is a pentameric immunoglobulin that is first produced in B cells in the early stage of infection, and is also called a representative natural antibody corresponding to the innate immune system.

IgG accounts for most of the immunoglobulins present in the serum and is produced in large quantities after IgM is produced during an immune response, and thus is also called a representative immunoglobulin of the adaptive immune system. IgA is an immunoglobulin mainly involved in local immunity because it exists in large amounts in mucosal secretions such as saliva, tear fluid, etc., in addition to serum, and IgE is involved in allergic diseases such as atopy.

Meanwhile, there are four isotypes of IgG: IgG1, IgG2, IgG3, and IgG4, out of which IgG3 may have a high degree of rotational freedom due to an extended hinge region transcribed from four exons and containing 11 disulfide bonds, and thus can bind to a wider range of antigens. Then, IgG3 is an IgG immunoglobulin having the most excellent binding affinity with various immune cells (dendritic cells, monocytes, granulocytes, macrophages, natural killer cells, etc.) as well as complement activating capacity after binding to antigens. In addition, IgG is known as a natural antibody firstly produced within a few hours at an initial stage of infection along with IgM, which corresponds to the innate immune system.

Natural antibodies perform various essential immune functions in the innate immune system. Firstly, the natural antibodies perform a protective function against various external infections such as bacteria, viruses, fungi, etc., including *S. pneumoniae*, sepsis, *Borrelia hermsii* bacteria, Influenza virus, *Listeria monocytogenes* bacteria, bullous stomatitis virus, lymphocytic choriomeningitis virus, *Cryptococcus neoformans* pathogens, and *Pneumocystis murina*. Secondly, natural antibodies play a role in regulating B-cell development, repertoire selection, and B-cell response, which are the core of adaptive immunity. Thirdly, natural antibodies are known to play a role in suppressing allergic reactions and protecting against cancer, as well as performing preventive protection against arteriosclerosis through the removal of apoptotic bodies and maintenance of vascular homeostasis. However, the number of B1 cells in the early stages of development, known to synthesize natural antibodies, decreases with age, and the expression of genes that promote immunoglobulin secretion also decreases, resulting in lower concentrations of IgM and IgG3 in the blood. In addition, a wide range of protective functions of natural antibodies against various external infectious agents come from the ability to recognize various epitopes present in phospholipids and oxidized lipids such as phosphorylcholine, which appear in bacterial cell walls, apoptotic cells, oxidized lipids, and the like, and glycoproteins and glycolipids present in exogenous structures derived from pathogens. This differs depending on an antibody repertoire constituting a variable region of an immunoglobulin heavy chain capable of binding to various epitopes. The variable region of the immunoglobulin heavy chain is formed by a combination of 38-46 variable (V) segments, 23 diversity (D) segments, and six joining (J) segments. The antibody repertoire capable of binding to all foreign antigens in the beginning is gradually reduced due to the learning of various antigens by vaccination after birth, an exposure to foreign infectious agents according to the living environment, etc. In other words, innate immunity, which has to play a role of primary protection against all external infections and activating subsequent adaptive immunity, inevitably continues to deteriorate after birth, but all current vaccines or antibody therapies merely activate the adaptive immune system to prevent or treat infectious diseases, without any attempts for activating the innate immune system.

Accordingly, the present inventor has focused on the formation of a fetal immune system during pregnancy in order to develop a treatment method for strengthening the innate immune system by natural antibodies. During pregnancy, a fetus is protected by a mother's immunoglobulin G, which is transmitted through an umbilical cord, which is formed around 15 weeks of pregnancy. However, it is not known precisely whether or not immunoglobulin formation is possible in fetuses before 15 weeks of pregnancy. It is known that a primordial form of B cell has been detected in the fetal liver from 8 weeks of gestation, but the development of B cells capable of forming antibodies on their own is possible after bone marrow is formed at 7 months of gestation, and it is also known that B cells are capable of forming antibodies in a T cell-dependent manner only after birth. However, considering that hematopoietic cells producing red blood cells are present in the aorta-gonad-mesonephros development site around 5 weeks of gestation, then pass through the placenta and are found in the liver and spleen at 3 months of gestation, the present inventor assumes that cells capable of producing natural antibodies for protecting the fetus from foreign infectious agents are also present in early pregnancy. Indeed, S. P. Loukogeorgakis (2017) has reported that fetal stem cells at the stage before embryonic stem cells differentiate into tridermal stem cells have pluripotency with long-term hematopoietic cell proliferation properties, A. Ditadi et al. (2009) have found that some of the fetal stem cells present in amniotic fluid express hematopoietic stem cell markers such as CD34 and CD133., M. D. Trapani et al. (2015) have disclosed that only fetal stem cells in early pregnancy express the CD34 hematopoietic stem cell marker, and fetal stem cells after mid-pregnancy lose their hematopoietic properties.

DISCLOSURE

Technical Problem

The present inventor has found that some immunoglobulin-containing extracellular vesicles are secreted from the fetal stem cells—previous 15 weeks of pregnancy, which were cultured under the in vitro culture conditions that mimic the body environment during pregnancy, which is capable of inducing the continuous secretion and expression of HLA-G protein for establishing an immune-tolerance environment to protect the fetus from a mother's immune system during pregnancy, according to US 2021-0147797 A1, which is incorporated herein by reference in its entirety. But, the inventor has also known that these extracellular vesicles do not contain IgG3 which plays a significant role in the innate immune system as a natural antibody. Accordingly, the present inventor has confirmed that extracellular vesicles containing various natural antibodies, such as IgG3 and IgM, and complement proteins capable of improving innate immunity can be obtained by applying extracellular vesicles derived from hematopoietic stem cells, which can be differentiated into B cells, and umbilical cord blood-derived stem cells to already established in vitro culture conditions that mimic in vivo environment during pregnancy, in order to promote immunoglobulin gene expression and secretion in fetal-derived stem cells.

Technical Solution

One object of the present invention is to provide fetal stem cell-derived extracellular vesicles with immune tolerance properties, containing immunoglobulins.

Another object of the present invention is to provide a method for preparing fetal stem cell-derived extracellular vesicles with immune tolerance properties, the method comprising: (a) obtaining trophoblast-derived extracellular vesicles having immune tolerance properties of secreting and expressing HLA-G; (b) obtaining extracellular vesicles through hypoxic co-culture of human hematopoietic stem cells and umbilical cord blood-derived mesenchymal stem cells; and (c) inoculating fetal stem cells into matrix gel for in vitro culture, and subculturing in a serum-free medium containing the trophoblast-derived extracellular vesicles of (a) and the extracellular vesicles derived from the co-culture of human hematopoietic stem cells and umbilical cord blood-derived mesenchymal stem cells of (b) under culture conditions of temperature change and vibration similar to those of the body during pregnancy.

Still another object of the present invention is to provide a pharmaceutical composition including the fetal stem cell-derived extracellular vesicles for preventing or treating infectious diseases caused by a foreign infectious agent.

Still another object of the present invention is to provide a composition including the fetal stem cell-derived extracellular vesicles for enhancing innate immunity.

Advantageous Effects

The extracellular vesicles containing fetal stem cell-derived primal immunoglobulins of the present invention contain various natural antibodies and complement proteins which can immediately respond to foreign infectious agents such as viruses, bacteria, pathogens, etc., and thus can effectively treat and prevent infectious diseases through an enhanced innate immune system, and can be also used to treat infectious diseases without side effects by promoting the production of antibodies that can be delivered to a patient's immune system and respond immediately to various foreign antigens.

BEST MODE

To achieve the above objects, one aspect of the present invention may provide the fetal stem cell-derived extracellular vesicles with immune tolerance properties, the extracellular vesicles comprising immunoglobulin M, immunoglobulin A, immunoglobulin D, immunoglobulin G, immunoglobulin G3, and immunoglobulin E.

The fetal stem cell-derived extracellular vesicles of the present invention may be cultured under in vitro culture conditions that mimic the body environment during pregnancy, thereby containing not only immunoglobulins including IgG3 and IgM capable of improving innate immunity, but also containing HLA-G protein resulting in exhibiting immune tolerance properties.

As used herein, the term "extracellular vesicles" refer to the vesicular bodies produced in a cell and secreted out of the cell, and includes exosomes, microvesicles, microparticles, etc., but are not limited thereto.

In the present invention, the fetal stem cell-derived extracellular vesicles may include various immunoglobulin proteins that play an essential role in innate immunity.

Specifically, the extracellular vesicles may include immunoglobulin M, immunoglobulin A, immunoglobulin D, immunoglobulin G, immunoglobulin G3, and immunoglobulin E.

By including the various immunoglobulin proteins, the extracellular vesicles may be used for the treatment of infectious diseases caused by external infectious agents by causing an immediate immune response to various foreign antigens such as viruses, bacteria, etc.

As used herein, the term "immunoglobulin M (IgM)" may be one of the antibodies produced by B cells, and may refer to an antibody that appears first when exposed to an antigen for the first time, which may exist as a pentamer or a hexamer via a disulfide bond between each monomer.

As used herein, the term "immunoglobulin A (IgA)" may be one of the antibodies produced by B cells, and may refer to an antibody mainly present in mucosal immunity, that is, mucosal secretions such as tears, saliva, sweat, colostrum, etc., and secretions of the gastrointestinal tract, prostate, and respiratory epithelium, and may be present as a monomer or a secreted dimer.

As used herein, the term "immunoglobulin D (IgD)" may be one of the antibodies produced by B cells and may refer to a monomeric antibody co-expressed with immunoglobulin M.

As used herein, the term "immunoglobulin E (IgE)" may be one of the antibodies produced by B cells and may refer to a monomeric antibody that mainly causes allergic and inflammatory reactions.

As used herein, the term "immunoglobulin G (IgG)" may be one of the antibodies produced by B cells and may refer to a monomeric antibody that accounts for 75% of the immunoglobulins present in the serum. As only one that passes through the placenta out of immunoglobulins, IgG may play a role in protecting the fetus in the womb along with IgA secreted into breast milk, and can play the most roles among antibodies participating in adaptive immunity through complement system activation and antibody-dependent cell-mediated cytotoxicity.

As used herein, the term "immunoglobulin G3 (IgG3)" may be one of four subtypes of IgG antibodies produced by B cells. Compared to other IgG antibody subtypes, immunoglobulin G3 may refer to an antibody with the highest degree of complement activity and affinity for Fc receptors present in immune cells. In addition, IgG3 is known to play a primary protective role from foreign antigens by participating in an initial immune response, that is, innate immunity together with IgM.

In one embodiment of the present invention, as a result of comparing the relative contents of immunoglobulins and protein components inducing the expression and secretion of immunoglobulins contained in various extracellular vesicles, it has been confirmed that all kinds of immunoglobulins and proteins promoting immunoglobulin synthesis are contained at a high level in fetal stem cell-derived extracellular vesicles having the above immune tolerance properties. Especially, it has been confirmed that IgG3, which plays a critical role in innate immunity, is contained only in the above fetal stem cell-derived extracellular vesicles.

The above fetal stem cell-derived extracellular vesicles having immune tolerance properties may further contain estrogen, octamer-binding protein 1 (OCT-1), octamer-binding protein 2 (OCT-2), nuclear factor kappa-light-chain-enhancer of activated B cells (NF-kB), immunoglobulin lambda-like polypeptide-1 (IGLL1), and cleavage stimulation factor (CstF).

In addition, the above extracellular vesicles may further contain complement subcomponent 1q (C1q), complement subcomponent 1r (C1r), complement subcomponent 1s (C1s), complement component 2 (C2), complement component 3 (C3), complement component 3a (C3a), complement component 4a (C4a), complement component 5/5a (C5/C5a), complement component 7 (C7), complement component 8 (C8) beta chain, complement component 9 (C9), complement factor B, complement factor mannose-binding lectin-associated serine protease-3 (MASP-3), interferon-induced transmembrane protein 3 (IFITM3), lymphocyte antigen 6 family member E (LY6E), and transient receptor potential cation channel, mucolipin subfamily, member 2 (TRPML2).

Furthermore, the above extracellular vesicles may further contain progesterone, human leukocyte antigen G1 (HLA-G1), human leukocyte antigen G2 (HLA-G2), human leukocyte antigen G5 (HLA-G5), and human leukocyte antigen G6 (HLA-G6) all.

As used herein, the term "estrogen" may refer to a hormone secreted from the ovaries and the placenta during pregnancy, and is known to play an important role in maintaining pregnancy together with progesterone. Estrogen may bind to an estrogen receptor, play a role in activating various transcription factors such as OCT1, NF-kB, etc., through a cyclin-D1 signaling pathway, and play a role in promoting the production of immunoglobulins in B lymphocytes.

As used herein, the term "octamer-binding protein 1 (OCT1)" may refer to one of the highly conserved transcription factor proteins that specifically bind to closely related sequences in an octamer motif (ATGCAAAT) and promoters and enhancers of various genes, and is known to be involved in various important biological functions such as embryonic development and neurogenesis. In particular, OCT1 may play a role in promoting the expression of immunoglobulin heavy chain genes by binding to the promoter and enhancer regions of the immunoglobulin heavy chain genes in early B cells.

As used herein, the term "octamer-binding protein 2 (OCT2)" may refer to one of the highly conserved transcription factor proteins that specifically bind to closely related sequences in an octamer motif (ATGCAAAT) and promoters and enhancers of various genes, and is known to be involved in various important biological functions such as embryonic development and neurogenesis. In particular, OCT2 may play a role in promoting the expression of immunoglobulin heavy chain genes by binding to the promoter and enhancer regions of the immunoglobulin heavy chain genes in mature B cells.

As used herein, the term "nuclear factor kappa-light-chain-enhancer of activated B cells (NF-kB)" may refer to a protein complex involved in the DNA transcription process, cytokine production, and cell survival. In particular, NF-kB may play an important role in inflammatory responses. In B cells, NF-kB may play a role in promoting transcription by activating the enhancer regions of the immunoglobulin heavy and light chain genes.

In the present invention, the estrogen, OCT1, OCT2, and NF-kB may serve to promote the transcription of immunoglobulin genes in target cells.

As used herein, the term "immunoglobulin lambda-like polypeptide-1 (IGLL1)," which is a protein expressed in the early stage of B cell development, may refer to a protein involved in the induction of a pre-B cell receptor (preBCR).

As used herein, the term "cleavage stimulation factor (CstF)" may refer to a protein involved in the cleavage of a signaling domain from a newly expressed pre-messenger ribonucleic acid (pre-mRNA) molecule. In particular, CstF may promote membrane-bound and secretory forms of IgM gene expression in B cells.

In the present invention, the IGLL1 and CstF may serve to promote the secretion of immunoglobulins including IgM in fetal stem cells.

As used herein, the term "complement," which is a part of the innate immune system, may refer to a protein which complements the functions of immune and phagocytic actions of attacking a cell membrane of pathogens by promoting an inflammatory response to remove external pathogens. A complement system may be activated by a classical pathway, an alternative pathway, and a lectin pathway.

As used herein, the term "complement subcomponent 1q (C1q)" may refer to a protein involved in the complement system of the innate immune system, and may play a role in forming a C1 complex by binding with the complement subcomponents 1r and is in a process of activating the complement system by the classical pathway following the formation of an antigen-antibody complex.

As used herein, the term "complement subcomponent 1r (C1r)" may refer to a protein involved in the complement system of the innate immune system, and may play a role in forming a C1 complex by binding with the complement subcomponents 1q and is in a process of activating the complement system by the classical pathway following the formation of an antigen-antibody complex.

As used herein, the term "complement subcomponent is (C1s)" may refer to a protein involved in the complement system of the innate immune system, and may play a role in forming a C1 complex by binding with the complement subcomponents 1q and 1r in a process of activating the complement system by the classical pathway following the formation of an antigen-antibody complex.

As used herein, the term "complement component 2 (C2)," which is a protein involved in a complement system of the innate immune system, may refer to a protein required for the formation of a complement component 3 (C3) convertase.

As used herein, the term "complement component 3 (C3)," which is a protein involved in a complement system of the innate immune system, may refer to a protein that play a central role in a process of complement activation by classical and alternative pathways.

As used herein, the term "complement component 3 (C3)," which is one of the proteins formed by cleavage of complement component 3 (C3) in the complement system of the innate immune system, may refer to a protein that binds to G protein-coupled receptor (GPCR), thereby activating the functions of various complement systems including T cell activation and proliferation, promotion of angiogenesis, chemotaxis, mast cell degranulation, and macrophage activation.

As used herein, the term "complement component 4a (C4a)," which is a non-enzymatic component protein of complement component 3 (C3) and complement component 5 (C5) convertases in the complement system of the innate immune system, may refer to a protein that promotes solubilization by effectively forming an amide bond with an immune aggregate and a protein antigen in a process of complement activation by a classical pathway.

As used herein, the term "complement component 5/5a (C5/C5a)," which is a protein involved in the complement system of the innate immune system, may refer to a protein underlying the formation of a membrane attack complex (MAC), in which activating peptide C5a cleaved by complement component 5 (C5) convertase has strong chemotactic activity, and C5b macromolecule forms a complex with complement component 6 (C6) to contain additional complement components.

As used herein, the term "complement component 7 (C7)" may refer to a protein which forms a membrane attack complex (MAC) with other complement components in the complement system of the innate immune system so as to puncture a pathogen surface, thereby causing the dissolution and death of pathogens.

As used herein, the term "complement component 8 (C8) beta chain" may refer to a protein which forms a membrane attack complex (MAC) with other complement components in the complement system of the innate immune system so as to puncture a pathogen surface, thereby causing the dissolution and death of pathogens.

As used herein, the term "complement component 9 (C9)" may refer to a protein in which 12-18 C9 molecular polymers form a membrane attack complex (MAC) with other complement components in the complement system of the innate immune system so as to puncture a pathogen surface, thereby causing the dissolution and death of pathogens.

As used herein, the term "complement factor B" may refer to a protein in which active peptide Bb produced by cleavage through complement factor D binds with C3b cleaved at complement factor 3 (C3) so as to form complement factor 3 (C3) convertase in a process of complement activation by an alternative pathway in the complement system of the innate immune system.

As used herein, the term "complement factor mannose-binding lectin-associated serine protease-3 (MASP-3)," which is a protein involved in the activation pathway of the complement system of the innate immune system, may refer to a protein that serves as a main enzyme activating a lectin pathway while playing a role in activating complement factor D in the alternative pathway.

As used herein, the term "interferon-induced transmembrane protein 3 (IFITM3)," which is a protein acting as an inhibitor against various viral infections including influenza, may refer to a protein which directly binds to the virus to block binding to a host cell receptor, inhibits the endocytosis of the virus bound to the receptor, and prevents the fusion between an enveloped virus membrane and an endosomal membrane, which enters the cell through acidic endosome, thereby preventing virus replication and moving the same to the lysosome to breaks down.

As used herein, the term "lymphocyte antigen 6 family member E (LY6E)," which is a protein known as a cell surface marker for differentiating immature thymocytes, may refer to a protein which plays a role in broadly limiting an initial entry of human coronavirus into a cell membrane.

As used herein, the term "transient receptor potential cation channel mucolipin subfamily member 2 (TRPML2)," which is a protein constituting a cation channel of the endosome, may refer to a protein which is up-expressed by a toll-like receptor (TLR) stimulation, a main receptor of innate immunity, and thus plays a role in inhibiting virus propagation through activation of antiviral autophagy.

In one embodiment of the present invention, as a result of analyzing a concentration of various complement proteins playing an essential role in innate immunity in the fetal stem cell-derived extracellular vesicles, it could be confirmed that they contain various complement proteins which are activated by immunoglobulins and thus responsible for the immediate innate immune system.

In another embodiment of the present invention, it could be confirmed that the fetal stem cell-derived extracellular vesicles contain various proteins performing an antiviral role.

In the present invention, the fetal stem cell-derived extracellular vesicles may be immune-tolerized or have immune tolerance properties in order to completely deliver active ingredients while avoiding an immune response caused by a patient's immune cells.

Specifically, as used herein, the term "immune tolerance" is also referred to as immunological tolerance, and may refer to a state in which an immune response by immune cells is not generated. Immune tolerance of the present invention may be established by secretion and expression of HLA-G protein, but is not limited thereto.

In one embodiment of the present invention, it has been confirmed that the extracellular vesicles contain progesterone that promotes the expression and secretion of HLA-G for inducing immune tolerance, thereby retaining immune tolerance properties.

In addition, in the present invention, the fetal stem cells or fetal-derived stem cells may be interchangeably used, and specifically may be derived from amniotic fluid, amniotic membrane, or umbilical cord blood, and more specifically may be amniotic fluid-derived fetal stem cells, but is not limited thereto.

In addition, the fetal stem cells may have immune tolerance properties of secreting and expressing HLA-G protein.

In one embodiment of the present invention, it could be confirmed that HLA-G1, G2, G5, and G6 mRNA are all expressed in the fetal stem cells, thereby having immune tolerance properties.

Another aspect of the present invention may provide a method for preparing fetal stem cell-derive extracellular vesicles with immune tolerance properties, the method comprising: (a) obtaining trophoblast-derived extracellular vesicles having immune tolerance properties of secreting and expressing HLA-G; (b) obtaining extracellular vesicles through hypoxic co-culture of human hematopoietic stem cells and umbilical cord blood-derived mesenchymal stem cells; and (c) inoculating fetal stem cells into matrix gel for in vitro culture, and subculturing in a serum-free medium containing the trophoblast-derived extracellular vesicles of (a) and the extracellular vesicles derived from the co-culture of human hematopoietic stem cells and umbilical cord blood-derived mesenchymal stem cells of (b) under culture conditions of temperature change and vibration similar to those of the body during pregnancy.

As used herein, the term "trophoblast" may refer to a cell which is a type of cell forming the placenta, provides signal transduction and nutrients involved in an embryonic development to an inner cell mass in the early stage of development, causes immune tolerance for protecting a fertilized embryo from a mother's immune system in the early stage of implantation, so as to induce successful implantation, and then forms the placenta to continuously express and secrete HLA-G protein, thereby playing an important role in the maintenance of pregnancy and the development of the fetus.

As used herein, the term "HLA-G protein" may refer to a protein called human leukocyte antigen G, HLA-G histocompatibility antigen class, G, or the like. Having been first discovered in extravillous trophoblast (EVT) cells present at a maternal-fetal interface during pregnancy, the HLA-G protein may be present as a membrane-bound form (HLA-G1, G2, G3, and G4 as membrane-bound HLA-G) expressed only in the cell membrane or as a soluble form that can be secreted out of the cell in a single molecule (HLA-G5, G6, and G7 as soluble HLA-G) by alternative splicing of HLA-G mRNA. In the present invention, the HLA-G protein may lower the toxicity of immune cells and promote the differentiation of regulatory T cells due to low polymorphism and specificity acting on immune cells, and thus is known to play an essential role in the establishment of an immune tolerance environment, in particular, protecting a fetus, which is an allograft, from a mother's immune system during pregnancy.

In addition, during pregnancy, the fetus may be present in amniotic fluid surrounded by an amniotic membrane, a fetal membrane may be composed of an amnion and a chorion in which trophoblast cells exist, and the placenta may consist of a chorion derived from the fetus and a decidual derived from the mother. Accordingly, the present inventor used a matrix gel for in vitro culture of trophoblast cells containing human amniotic fluid and amniotic membrane stem cell-derived extracellular vesicles to simulate the fetal membrane structure during pregnancy in vitro, thereby obtaining fetal stem cell-derived extracellular vesicles under conditions similar to those of the body environment during pregnancy.

Through the above production method, extracellular vesicles derived from hematopoietic stem cells, which may be differentiated into B cells, and umbilical cord blood-derived stem cells were applied to in vitro culture conditions that mimic the in vivo environment during pregnancy, so as to promote the expression and secretion of immunoglobulin genes in fetal stem cells, thereby preparing the fetal stem cell-derived extracellular vesicles with immune tolerance properties.

The method for preparing fetal stem cell-derived extracellular vesicles having immune tolerance properties may further include:

(d) inoculating the subcultured fetal stem cells into a culture plate and culturing in a serum-free medium, so as to obtain a culture supernatant; and (e) multi-step filtering the culture supernatant and isolating the extracellular vesicles.

In addition, the trophoblast-derived extracellular vesicles with immune tolerance properties of secreting and expressing HLA-G of (a) of the above preparation method may include:

(a-1) obtaining extracellular vesicles through co-culture of human amniotic membrane-derived mesenchymal stem cells and amniotic fluid-derived mesenchymal stem cells;

(a-2) inoculating human trophoblast cells into a matrix gel for in vitro culture containing hyaluronic acid in the above extracellular vesicles; and (a-3) culturing the trophoblast cells under culture conditions of temperature change and vibration similar to those of the body during pregnancy.

Specifically, the above (a-1) may include:

(a-1-1) freeze-storing human amniotic membrane and amniotic fluid-derived mesenchymal stem cells in a cryopreservation composition containing 5 to 50% (v/v) of immune-tolerized human mesenchymal stem cell-derived extracellular vesicles; and (a-1-2) thawing the cryopreserved human amniotic membrane and amniotic fluid-derived mesenchymal stem cells, inoculating them into each of lower and upper wells of a co-culture plate, and co-culturing them in a serum-free medium to obtain a culture supernatant, but is not limited thereto.

In addition, the extracellular vesicles and hyaluronic acid in the above (a-1) may be mixed at a weight ratio of 1:1 to 1:20 so as to prepare a matrix gel for in vitro culture.

Furthermore, in (a-1), the trophoblast cells may be inoculated at a density of 5,000 to 15,000 cells/cm$^2$.

Moreover, specifically, the above (a-2) and (a-3) may include mixing hyaluronic acid and extracellular vesicles obtained by multi-step filtering the culture supernatant and isolation so as to prepare a matrix gel for in vitro culture, and inoculate human trophoblast cells thereto so as to subculture in a serum-free medium, but is not limited thereto.

In addition, the trophoblast cells subcultured in (a-3) may be inoculated at a density of 10,000 to 30,000 cells/cm$^2$ in a normal culture plate after washing, so as to obtain a culture supernatant after serum-free culture for 72 to 120 hours.

Furthermore, in addition to the above step, there may be included (a-4) multi-step filtration of the culture supernatant obtained by inoculating the subcultured trophoblast cells in a culture plate and then culturing in a serum-free manner, and isolation of the extracellular vesicles.

In this case, the culture supernatant may be filtered by performing 1 to 10 times, preferably 4 times, using a filter of 0.3 μm to 1 μm, specifically 0.45 μm to 0.8 μm. In one embodiment, the culture supernatant may be filtered by performing 0.8 μm filtering and 0.45 μm filtering twice, respectively, but is not limited thereto.

The trophoblast-derived extracellular vesicles having immune tolerance properties of secreting and expressing HLA-G, obtained by the method of (a), may contain HLA-G1, HLA-G2, HLA-G5, and HLA-G6 proteins for inducing immune tolerance, progesterone for promoting mRNA expression of HLA-G gene, and estrogen for promoting mRNA expression of immunoglobulin genes.

In addition, the extracellular vesicles obtained through hypoxic co-culture of human hematopoietic stem cells and umbilical cord blood-derived mesenchymal stem cells of step (b) of the preparation method may be prepared by:

(b-1) inoculating human hematopoietic stem cells and umbilical cord blood-derived mesenchymal stem cells in the upper and lower wells of a co-culture plate, respectively;

(b-2) co-culturing them in a serum-free medium under 1 to 5% $O_2$ hypoxic conditions to obtain a culture supernatant; and (b-3) multi-stage filtering the culture supernatant and isolating the extracellular vesicles.

Specifically, the above (b-1) may include:

(b-1-1) freeze-storing human hematopoietic stem cells and umbilical cord blood-derived stem cells in a cryopreservation composition containing 5 to 50% (v/v) of immune-tolerized human mesenchymal stem cell-derived extracellular vesicles; and (b-1-2) thawing the cryopreserved human hematopoietic stem cells and umbilical cord blood-derived stem cells, and inoculating them into each of the lower and upper wells of a co-culture plate, but is not limited thereto.

Specifically, when it comes to an inoculation density, human hematopoietic stem cells and umbilical cord blood-derived mesenchymal stem cells may be inoculated at a density of 5,000 to 15,000 cells/cm$^2$, respectively, in the above (b-1-1), while human hematopoietic stem cells and umbilical cord blood-derived mesenchymal stem cells may be inoculated at a density of 18,000 to 22,000 cells/cm$^2$, respectively, in the above (b-1-2), but is not limited thereto.

In addition, the co-culture of the above (b-1) may be performed for 100 to 140 hours, specifically, 114 to 126 hours, but is not limited thereto.

Furthermore, in the above (b-3), the culture supernatant may be filtered by performing 1 to 10 times, preferably 4 times, using a filter of 0.3 μm to 1 μm, specifically 0.45 μm to 0.8 μm. In one embodiment, the culture supernatant may be filtered by performing 0.8 μm filtering and 0.45 μm filtering twice, respectively, but is not limited thereto.

In addition, the extracellular vesicles obtained through hypoxic co-culture of human hematopoietic stem cells and umbilical cord blood-derived mesenchymal stem cells of step (b) of the preparation method may contain:

octamer-binding protein 2 (OCT2) for promoting an expression of immunoglobulin genes in fetal stem cells, immunoglobulin lambda-like polypeptide-1 (IGLL1) and a cleavage stimulation factor (CstF) for promoting secretion of immunoglobulin.

Furthermore, the matrix gel for in vitro culture of the above (c) may contain: extracellular vesicles obtained through co-culture of human amniotic membrane-derived mesenchymal stem cells and amniotic fluid-derived mesenchymal stem cells and hyaluronic acid.

Specifically, the matrix gel for in vitro culture may maintain an acidic condition of pH 6 to 7 by adding hyaluronic acid.

In addition, the culture conditions of temperature change and vibration similar to those of the body during pregnancy in the above (c) may be conditions of temperature change in a five-day cycle changed within a range of 36.0° C. to 37.0° C. based on a basal body temperature method and conditions of vibration culture at a 24-hour cycle changed within a range of 0 RPM to 60 RPM.

Specifically, the temperature change condition may be a temperature change condition that changes to 36.5° C. in 0 to 12 hours, 36.4° C. in 12 to 36 hours, 36.3° C. in 36 to 48 hours, 36.2° C. in 48 to 60 hours, 36.0° C. in 60 to 72 hours, and 37.0° C. in 72 to 120 hours, but is not limited thereto.

Specifically, the vibration culture condition may be a vibration culture condition that changes to 0 RPM in 0 to 7 hours, 30 RPM in 8 hours, 60 RPM in 9 to 18 hours, 20 RPM in 19 hours, and 0 RPM in 20 to 24 hours, but is not limited thereto.

The fetal stem cell-derived extracellular vesicles having immune tolerance properties obtained through the above preparation method may include IgG, IgA, IgM, IgE, IgD, and IgG3.

Still another aspect of the present invention may provide a pharmaceutical composition, including the fetal stem cell-derived extracellular vesicles with immune tolerance properties, for preventing or treating infectious diseases caused by a foreign infectious agent.

In one embodiment of the present invention, it could be confirmed that a concentration of IgG3 and IgM is remarkably increased with respect to foreign antigens upon treatment with the above fetal stem cell-derived extracellular vesicles, which may be used for preventing and treating infectious diseases by promoting the production of antibodies associated with innate immunity.

As used herein, the term "prevention" may refer to all the acts, which inhibit or delay infection and infectious disease caused by foreign infectious agents by using extracellular vesicles according to the present invention.

As used herein, the term "treatment" may refer to all the acts, by which a symptom of infectious diseases caused by a foreign infectious agent gets better or takes a favorable turn by using extracellular vesicles according to the present invention.

In the pharmaceutical composition for preventing or treating infectious diseases of the present invention, the route and mode for administration of the composition are not particularly limited, but any route and mode of administration may be followed as long as the composition reaches a corresponding target site. Specifically, the composition may be administered through a variety of oral or parenteral routes, and non-limiting examples of the route of administration may include oral, topical, intravenous, intraperitoneal, intramuscular, intraarterial, transdermal, intranasal administrations, or through inhalation, etc. In addition, the composition may be administered by any device capable of moving an active substance to a target cell.

As used herein, the term "foreign infectious agent" may refer to microorganisms that cause diseases in the body of humans or animals, such as viruses, bacteria, fungi, parasites, pathogens, etc., but is not limited thereto.

Specifically, the virus may be Orthomyxoviridae genus virus, Picorna viridae genus virus, Retroviridae genus virus, Filoviridae genus virus, Coronaviridae genus virus, Hepadnaviridae genus virus, Flaviviridae genus virus, Bunyaviridae genus virus, Herpes genus virus, etc., but is not limited thereto.

In addition, specifically, the bacteria may be *Streptococcus* genus, *Borrelia* genus, *Listeria* genus bacteria, etc., but is not limited thereto.

In addition, the fungus may be *Pneumocystis* genus, *Cryptococcus* genus, etc., but is not limited thereto.

As used herein, the term "infectious disease" may refer to all the diseases caused by a foreign infectious agent spreading to or invading animals or humans.

In one specific embodiment, all the diseases that may be caused by viruses, bacteria, fungi, etc., which are the infectious agent, may be included without limitation.

In addition, as another specific embodiment, the diseases caused by *S. pneumoniae, Borrelia hermsii, Listeria monocytogenes, Cryptococcus neoformans, Pneumocystis murina*, Influenza, etc., may be included, but are not limited thereto.

In the present invention, the pharmaceutical composition for preventing or treating infectious diseases may further include a pharmaceutically acceptable carrier, excipient or diluent commonly used in the preparation of the pharmaceutical composition, and the carrier may include a non-naturally occurring carrier.

In the present invention, the term "pharmaceutically acceptable" may refer to exhibiting non-toxic properties to cells or humans exposed to the composition.

More specifically, the pharmaceutical composition may be formulated in the form of oral formulations such as powders, granules, tablets, capsules, suspensions, emulsions, syrups, aerosols, etc.; external preparations; suppositories; and sterile injection solutions according to each conventional method, but is not limited thereto, as long as the formulation is used for the prevention or treatment of infectious diseases in the art.

The carrier, excipient, and diluent, which may be included in the pharmaceutical composition, for specific example, may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, polycaprolactone (PCL), polylactic acid (PLA), poly-L-lactic acid (PLLA), mineral oil, etc.

In case of formulating a preparation, the preparation may be prepared by using diluents or excipients such as fillers, extenders, binders, humectants, disintegrants, surfactants, etc., which are generally used.

A solid preparation for oral administration may include tablets, pills, powders, granules, capsules, etc., and these solid preparations may be prepared by mixing at least one excipient, for example, starch, calcium carbonate, sucrose, lactose, gelatin or the like in the extract and fractions thereof. In addition, lubricants such as magnesium stearate and talc may be also used in addition to simple excipients.

A liquid preparation for oral administration may include suspending agents, liquids for internal use, emulsions, syrups, etc., but may also include several excipients, for example, humectants, sweetening agents, flavoring agents, preservatives, etc. in addition to water and liquid paraffin, which are the frequently used simple diluents. A preparation for non-oral administration may include a sterilized aqueous solution, non-aqueous solvent, suspending agent, emulsion, freeze-dried preparation, suppository, etc. As the non-aqueous solvent and the suspending agent, propylene glycol, polyethylene glycol, vegetable oil like olive oil, injectable ester like ethyl oleate, etc. may be used. A base of the suppository used herein may include witepsol, macrogol, tween 61, cacao butter, laurinum, glycerogelatin, etc.

Still another aspect of the present invention may provide a composition for enhancing innate immunity, including the fetal stem cell-derived extracellular vesicles having immune tolerance properties.

As used herein, the term "innate immunity" may refer to an immune system that non-specifically and immediately responds to a non-self-antigen without discrimination of a specific pathogen. In one embodiment of the present application, it could be confirmed that there is an effect of remarkably increasing a concentration of IgG3 and IgM with respect to foreign antigens upon the treatment with the fetal stem cell-derived extracellular vesicles, which may be used for enhancing innate immunity.

The composition for enhancing innate immunity may be a health functional food, cosmetic, quasi-drug, or feed composition.

As used herein, the term "health functional food" may be the same term as food for special health use (FoSHU), and refer to the food having a high medical and medicinal effect, which is processed to efficiently show a biological regulation function in addition to supplying nutrients. In the present invention, the health functional food may be used in a mixed way with health food or health supplement.

As used herein, the term "cosmetics" may refer to articles used on the human body to clean and beautify the human body to add attractiveness, to brighten the appearance, or to maintain or promote skin and hair health, thus meaning that the cosmetics have a slight effect on the human body. The term may also include the meaning of functional cosmetics that help whiten the skin, help reduce wrinkles on the skin, tan the skin finely, or help protect the skin from UV rays.

As used herein, the term "quasi-drug" may refer to articles with a milder action than pharmaceuticals among articles used for the purpose of diagnosing, curing, ameliorating, alleviating, treating, or preventing diseases of humans or animals. For example, quasi-drugs according to the Pharmaceutical Affairs Act may exclude products used for medicinal purposes, including products used for the treatment or prevention of diseases of humans/animals, and products with minor or no direct action on the human body.

As used herein, the term "feed" may refer to any natural or artificial diet, one meal, etc., or an ingredient of the one meal, which is to be eaten, consumed or digested by livestock or appropriate thereto.

Still another aspect of the present invention may provide the use of fetal stem cell-derived extracellular vesicles having the immune tolerance properties for preventing or treating infectious diseases caused by foreign infectious agents.

Still another aspect of the present invention may provide the use of fetal stem cell-derived extracellular vesicles having the immune tolerance properties for enhancing innate immunity.

MODE FOR INVENTION

Hereinafter, the configuration and effects of the present invention will be described in more detail through Examples. The following Examples are provided only for the purpose of illustrating the present invention, and thus the scope of the present invention is not limited thereto.

Example 1: Preparation of the Ex Vivo Matrix Gel for Trophoblast Cell Culture for Induction of Immune Tolerance Properties and Acquisition of Trophoblast-Derived Extracellular Vesicles (itTBC-EVs) with Immune Tolerance Properties A matrix gel was prepared for ex vivo culture of trophoblast cells capable of inducing immune tolerance properties.

More specifically, in order to exclude heterologous antigens that may be contained in extracellular vesicles, human amniotic membrane-derived mesenchymal stem cells (SciEnCell, Cat. #7140) and amniotic fluid-derived mesenchymal stem cells established from amniotic fluid sample donated from a healthy mother were stored at −80° C. in a cryogenic freezer for three weeks with cryopreservation composition containing immune-tolerized human mesenchymal stem cell-derived extracellular vesicles (MBTC-MSC-EXO, Stemmedicare) in place of fetal bovine serum (FBS). After thawing each of the stored stem cells, for co-culture, the amniotic membrane-derived mesenchymal stem cells were dispensed in a lower plate of a multi dish (ThermoFisher Scientific Inc., Rockford, IL USA, Cat. #140663), and the amniotic fluid-derived mesenchymal stem cells were dispensed in an upper insert at a density of 20,000 cells/cm$^2$ with a serum-free DMEM/F12 medium, respectively, and co-cultured at 37° C., 5% $CO_2$ incubator for 120 hours. Then, the culture supernatant was collected and filtered twice using 0.8 μm and 0.45 μm filter, respectively, so as to obtain the co-cultured extracellular vesicles of human amniotic fluid- and amniotic membrane-derived mesenchymal stem cells (AF/AM-MSC$^{CO}$-EVs).

Hyaluronic acid was added to a concentrated solution of co-cultured extracellular vesicles of human amniotic fluid- and amniotic membrane-derived mesenchymal stem cells obtained as described above in the method so that pH reaches 6.6 to 6.8 and mixed using a vortex mixer to prepare the ex vivo matrix gel, which was then dispensed in a culture plate, shaken on a vibrator to be evenly distributed, then trophoblast cells were dispensed on the gel and subcultured in a serum-free DMEM/F12K medium at intervals of 5-6 days.

In this case, in order to induce the secretion of progesterone and estrogen hormones from trophoblast cells, the temperature change condition of a 5-day cycle within the range of 36.0° C. to 37.0° C. similar to the change in body temperature of women before and after ovulation (FIG. 2), and the vibratory culture condition of a 24-hour cycle varying within the range of 0 RPM to 60 RPM range (FIG. 3) were applied.

In addition, in order to confirm that trophoblast cells cultured on the ex vivo matrix gel can continuously secrete HLA-G protein, a concentration of soluble HLA-G (sHLA-G) protein in the culture supernatant obtained during each subculture was measured with the Human HLA-G ELISA kit (LSBio) using the MEM-G/9 antibody while carrying out a subculture. When the sHLA-G concentration of the culture supernatant exceeded 20 ug/ml for at least three passages, it was regarded as immune-tolerized trophoblast cells (it-TBCs) and the subculture was stopped.

Immune-tolerized trophoblast cells cultured on the ex vivo matrix gel were dispensed at a density of 15,000 cells/cm$^2$ in serum-free DMEM/F-12K medium by using a general culture plate and cultured in 37° C., 5% $CO_2$ incubator for 96 hours to collect a culture supernatant, which was then filtered twice using 0.8 μm and 0.45 μm filter, respectively, so as to isolate and obtain trophoblast-derived extracellular vesicles (itTBC-EVs) with immune tolerance properties containing HLA-G protein.

Example 2: Acquisition of Co-Cultured Extracellular Vesicles of Human Hematopoietic Stem Cells and Umbilical Cord Blood-Derived Mesenchymal Stem Cell HSC/UCB-MSC$^{CO}$-EVs A co-culture system of human hematopoietic stem cells and umbilical cord blood-derived mesenchymal stem cells was developed to obtain extracellular vesicles capable of inducing innate immune properties.

More specifically, in order to exclude heterologous antigens that may be contained in extracellular vesicles, human hematopoietic stem cells (Promocell, Cat. #C-28021) and human umbilical cord blood-derived mesenchymal stem cells (Cyagen, Cat. #HUXUB-01001) were stored at −80° C. in a cryogenic freezer for three weeks with cryopreservation composition containing human mesenchymal stem cell-derived extracellular vesicles in place of fetal bovine serum (FBS). After thawing each of the stored stem cells, for co-culture, the umbilical cord blood-derived mesenchymal stem cells were dispensed in a lower plate of a multi-dish at a density of 20,000 cells/cm$^2$, and the human hematopoietic stem cells were dispensed in an upper insert at a density of 50,000 cells/cm² with a serum-free DMEM/F12 medium, respectively, and co-cultured at 37° C., 5% $CO_2$ incubator for 72 hours under 5% hypoxic condition. Then, the culture supernatant was collected and filtered twice using 0.8 μm and 0.45 μm filter, respectively, so as to obtain the co-cultured extracellular vesicles of human hematopoietic stem cells and umbilical cord blood-derived mesenchymal stem cells (HSC/UCB-MSC$^{CO}$-EVs).

Example 3: Method for Preparing Fetal Stem Cell-Derived Extracellular Vesicles (itPG-EVs) Containing Various Primal Immunoglobulins An attempt was made to prepare fetal stem cell derived-extracellular vesicles containing primal immunoglobulins of the present invention.

Figure 1:
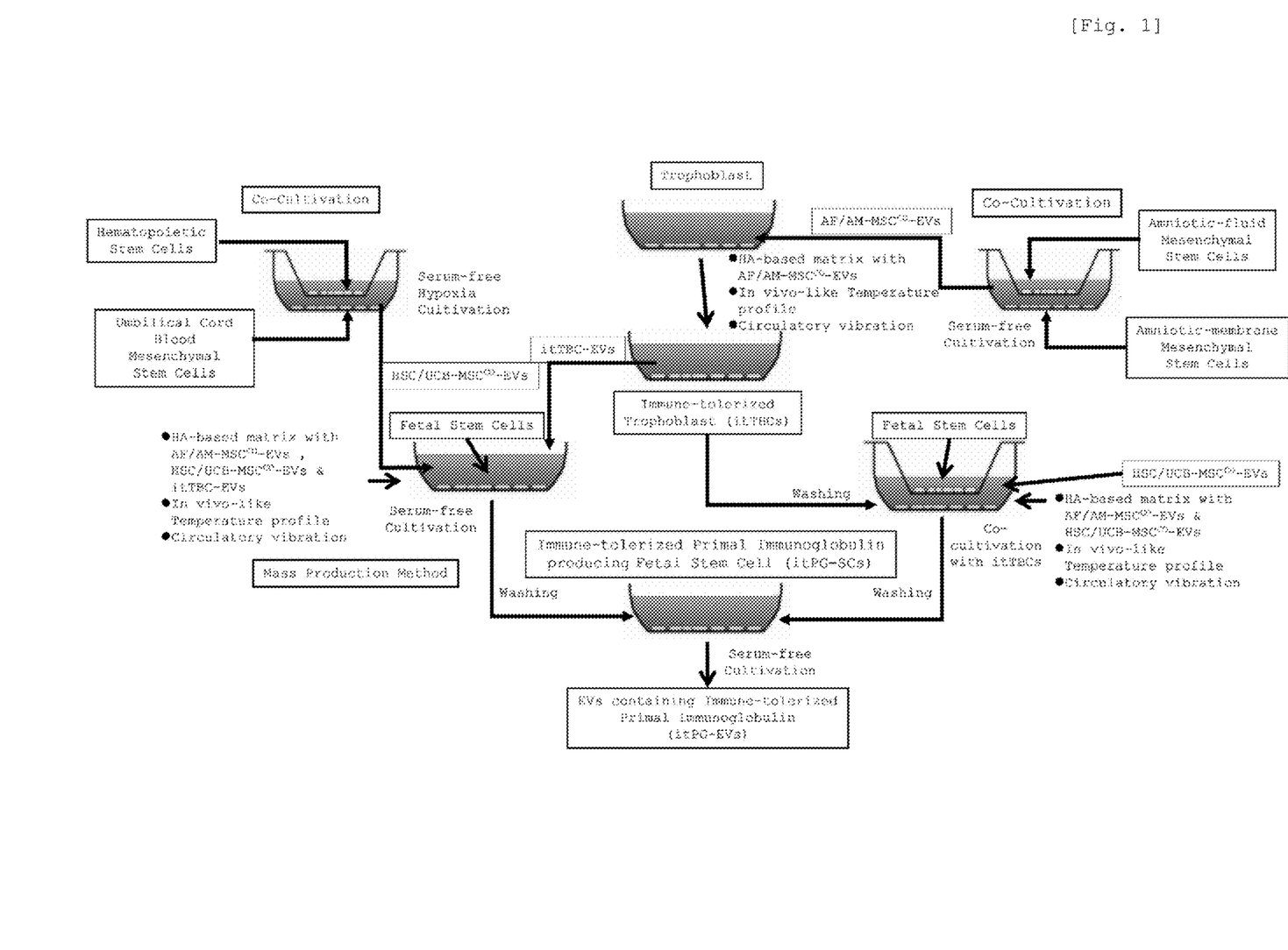
FIG. 1 is a schematic view of a production process of extracellular vesicles containing fetal stem cell-derived primal immunoglobulins.
Figure 2:
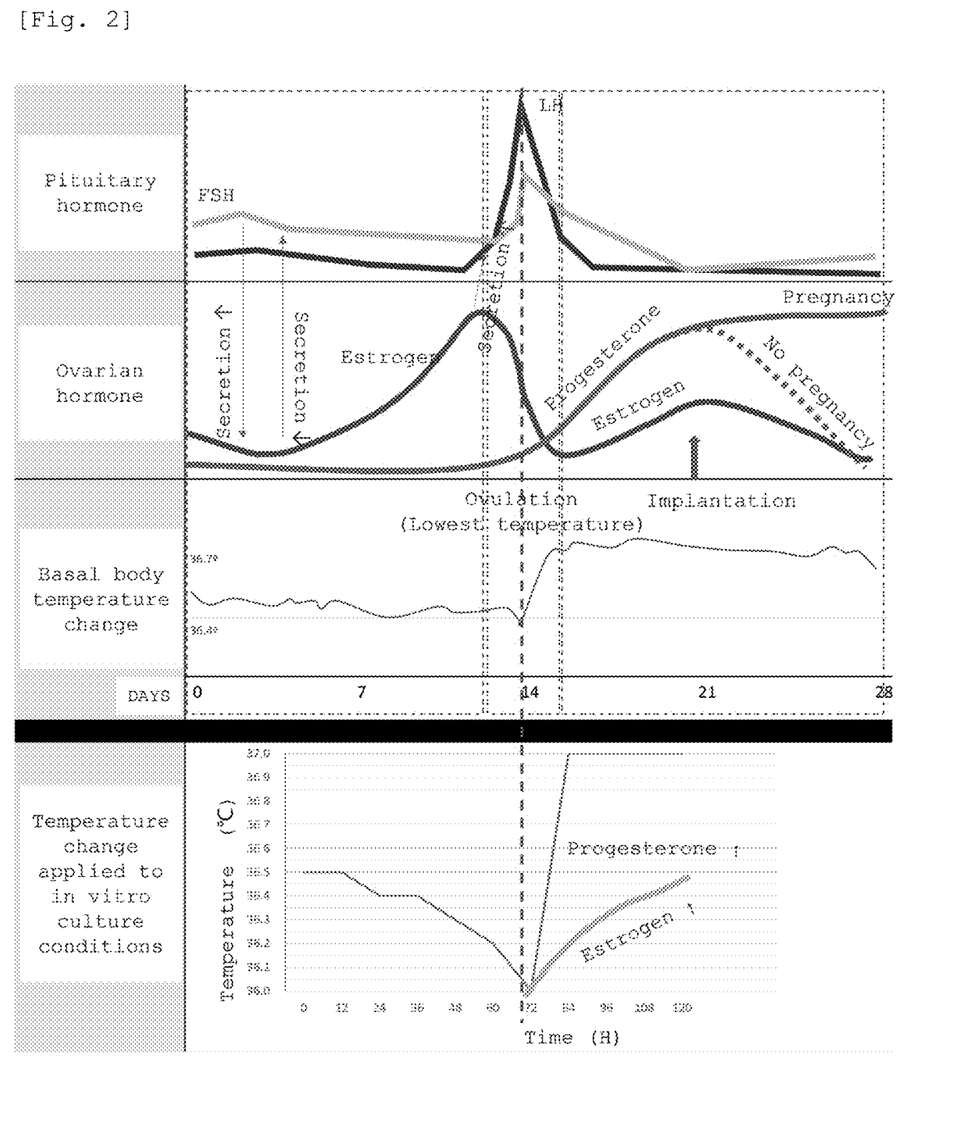
FIG. 2 shows the temperature change conditions of a five-day cycle within a range of 36.0° C. to 37.0° C. similar to a change in body temperature of women before and after ovulation applied to a culture process for inducing secretion of progesterone and estrogen hormones from trophoblast and fetal stem cells.
Figure 3:
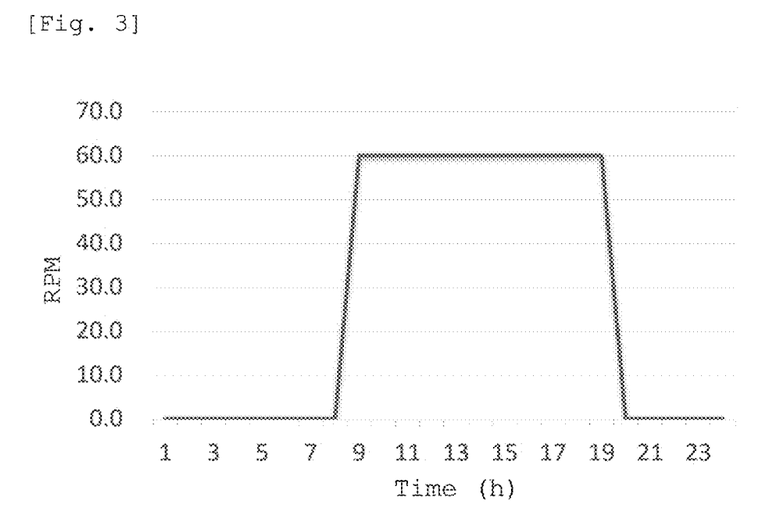
FIG. 3 shows the vibratory culture conditions of a 24-hour cycle varying within a range of 0 RPM to 60 RPM applied to a culture process in order to promote the secretion and circulation of various soluble factors from trophoblast and fetal stem cells.

More specifically, in order to induce the secretion of extracellular vesicles containing various immunoglobulins and complement proteins involved in innate immunity in target cells, fetal-derived stem cells (hFSCs) isolated from amniotic fluid were inoculated into the culture plate in which the ex vivo matrix gel prepared in Example 1 was dispensed, and cultured in a serum-free DMEM/F-12 containing each 10% (v/v) of trophoblast-derived extracellular vesicles (itTBC-EVs) with induced immune tolerance properties of constantly secreting and expressing HLA-G protein of Example 1 and extracellular vesicles (HSC/UCB-MSC$^{CO}$-EVs) obtained through co-culture of human hematopoietic stem cells and umbilical cord blood-derived mesenchymal stem cells of Example 2, respectively. In order to activate the expression of estrogen for promoting the expression of immunoglobulin genes, and progesterone for promoting the expression of HLA-G, which induces immune tolerance, in target cells, subcultures were performed in an incubator at 37° C. and 5% $CO_2$ environment by applying the temperature change condition of a 5-day cycle as shown in FIG. 2 and the vibration condition as shown in FIG. 3.

In order to confirm that fetal-derived stem cells cultured on the ex vivo matrix gel can continuously secrete HLA-G protein, a concentration of soluble HLA-G (sHLA-G) protein in the culture supernatant obtained during each subculture was measured with the Human HLA-G ELISA kit (LSBio) using the MEM-G/9 antibody while carrying out a subculture. When the sHLA-G concentration of the culture supernatant exceeded 20 ug/ml for at least three passages, it was regarded as immune-tolerized fetal stem cells (itFSCs) and the subculture was stopped. The immune-tolerized fetal-derived stem cells cultured in the ex vivo matrix gel were washed and inoculated at a density of 2.0×10⁴ cells/cm² in a normal plate without the ex vivo matrix gel, and then incubated with a serum-free DMEM/F-12 medium in 37° C., 5% $CO_2$ incubator for 120 hours. The collected culture supernatant was filtered twice using 0.8 μm and 0.45 μm filter, respectively, so as to obtain the isolated immune-tolerized primal immunoglobulin-containing extracellular vesicles (itPG-EVs).

The content of immunoglobulins contained in the extracellular vesicles (itPG-EVs) obtained through the above culture was quantitatively analyzed with each ELISA kit. As a result, it could be confirmed that all kinds of immunoglobulins are contained as shown in table 1, and in particular, it could be confirmed that IgG3, playing an important role as a natural antibody in innate immunity, is also contained along with IgM. In addition, it could be confirmed that extracellular vesicles also contain IgA, which plays an important role in governing an initial neutralizing antibody response to viruses that cause respiratory infections, such as COVID-19.

TABLE 1

Concentration of immunoglobulins contained in immune-tolerized extracellular vesicles (itPG-EVs) containing primal immunoglobulins

| Immunoglobulin | Concentration(ng/ml) |
| --- | --- |
| Immunoglobulin G | 12.31 ± 2.64 |
| Immunoglobulin A | 6.78 ± 1.22 |
| Immunoglobulin M | 1.38 ± 0.29 |
| Immunoglobulin E | 0.94 ± 0.16 |
| Immunoglobulin D | 0.042 ± 0.003 |
| Immunoglobulin G3 | 0.55 ± 0.03 |

In addition, the relative contents of immunoglobulins and protein components inducing the expression and secretion of immunoglobulins contained in the immune-tolerized extracellular vesicles (itPG-EVs) containing primal immunoglobulins were compared with those of trophoblast-derived extracellular vesicles with immune tolerance properties (itTBC-EVs) of Example 1, co-cultured extracellular vesicles of hematopoietic stem cells and umbilical cord blood-derived mesenchymal stem cells having the innate immune properties of Example 2 (HSC/UCB-MSC$^{CO}$-EVs), immune-tolerized fetal stem cell-derived extracellular vesicles (itFSC-EVs) cultured in the same culture conditions as in Example 3 with a medium containing only the trophoblast-derived extracellular vesicles (itTBC-EVs) having the immune tolerance properties of Example 1 (itFSC-EVs), and non-immune-tolerized fetal stem cell-derived extracellular vesicles (FSC-EVs) cultured under normal stem cell culture conditions rather than the culture conditions using the trophoblast cells. As a result, it was confirmed that no immunoglobulin is detected in itTBC-EVs and HSC/UCB-MSC$^{CO}$-EVs and some immunoglobulins are detected at low levels in itFSC-EVs and FSC-EVs, but the itPG-EVs of the present invention contain much higher levels of all kinds of immunoglobulins. In particular, it could be confirmed that IgD and IgG3, which plays an important role in innate immunity, are contained only in itPG-EVs. In addition, it could be confirmed that itPG-EVs also contain much higher levels of components such as estrogen, octamer-binding protein 1 (OCT-1), octamer-binding protein 2 (OCT-2), and nuclear factor kappa-light-chain-enhancer of activated B cells (NF-kB), which promote the expression of immunoglobulin genes in target cells. It could be also confirmed that itPG-EVs also contain much higher levels of immunoglobulin lambda-like polypeptide-1 (IGLL1) and cleavage stimulation factor (CstF), which stimulate immunoglobulin synthesis in target cells.

TABLE 2

Comparison of relative contents of immunoglobulins and protein components inducing the expression and secretion of immunoglobulins contained in various extracellular vesicles as obtained in Examples 1, 2, and 3

| Protein | itPG-EVs | itTBC-EVs | HSC/UCB-MSC$^{CO}$-EVs | itFSC-EVs | FSC-EVs |
| --- | --- | --- | --- | --- | --- |
| IgG | 1.00 | No-detection | No-detection | 0.67 | 0.39 |
| IgA | 1.00 | No-detection | No-detection | 0.66 | 0.32 |

TABLE 2-continued

Comparison of relative contents of immunoglobulins and protein components inducing the expression and secretion of immunoglobulins contained in various extracellular vesicles as obtained in Examples 1, 2, and 3

| Protein | itPG-EVs | itTBC-EVs | HSC/UCB-MSC$^{CO}$-EVs | itFSC-EVs | FSC-EVs |
|---|---|---|---|---|---|
| IgM | 1.00 | No-detection | No-detection | 0.58 | 0.17 |
| IgE | 1.00 | No-detection | No-detection | 0.68 | 0.53 |
| IgD | 1.00 | No-detection | No-detection | No-detection | No-detection |
| IgG3 | 1.00 | No-detection | No-detection | No-detection | No-detection |
| CstF | 1.00 | 0.34 | 0.47 | 0.55 | 0.48 |
| IGLL1 | 1.00 | 0.18 | 0.38 | 0.58 | 0.16 |
| OCT1 | 1.00 | 0.64 | No-detection | 0.76 | 0.61 |
| OCT2 | 1.00 | 0.16 | 0.49 | 0.68 | 0.48 |
| Estrogen | 1.00 | 0.73 | No-detection | 0.87 | No-detection |
| NF-κB | 1.00 | 0.26 | 0.64 | 0.71 | 0.54 |

In addition, the concentrations of various complement proteins, playing an essential role in innate immunity, contained in the immune-tolerized extracellular vesicles (itPG-EVs) containing primal immunoglobulin were analyzed, and then it was confirmed that various complement proteins, activated by primal immunoglobulins and serving as the immediate innate immune system, are contained as shown in table 3.

TABLE 3

Concentration of complement proteins contained in the immune-tolerized extracellular vesicles (itPG-EVs) containing primal immunoglobulins

| Complement protein | Concentration(ng/ml) |
|---|---|
| Complement C1r subcomponent | 2.94 ± 0.46 |
| Complement C1s subcomponent | 1.24 ± 0.37 |
| Complement C2 | 0.82 ± 0.16 |
| Complement C3 | 12.15 ± 2.43 |
| Complement C3a | 0.13 ± 0.02 |
| Complement C4a | 4.56 ± 0.76 |
| Complement C5/C5a | 3.06 ± 0.43 |
| Complement C7 | 1.30 ± 0.21 |
| Complement C8 beta chain | 2.79 ± 0.68 |
| Complement C9 | 0.28 ± 0.06 |
| Complement factor B | 2.11 ± 0.45 |
| Complement factor MASP-3 | 0.94 ± 0.19 |

And the concentrations of antiviral proteins contained in the immune-tolerized extracellular vesicles (itPG-EVs) containing primal immunoglobulins were analyzed, and then it was confirmed that various antiviral proteins, inhibiting the entry and replication of viruses in the cell membrane and endosome membrane, are contained as shown in table 4.

TABLE 4

Concentrations of antiviral proteins contained in the immune-tolerized extracellular vesicles (itPG-EVs) containing primal immunoglobulins

| Antiviral protein | Concentration (ng/50 ug of EVs) |
|---|---|
| Interferon-induced transmembrane family member protein 3 | 12.38 ± 4.17 |
| Lymphocyte antigen 6 family member E | 55.75 ± 10.05 |

TABLE 4-continued

Concentrations of antiviral proteins contained in the immune-tolerized extracellular vesicles (itPG-EVs) containing primal immunoglobulins

| Antiviral protein | Concentration (ng/50 ug of EVs) |
|---|---|
| Transient receptor potential cation channel, mucolipin subfamily, member 2 | 3.12 ± 1.86 |

Example 4: Efficacy of Inducing Antibody Production of the Immune-Tolerized Extracellular Vesicles Containing Primal Immunoglobulins In order to confirm the efficacy of enhancing innate immunity of the immune-tolerized extracellular vesicles (itPG-EVs) containing primal immunoglobulins prepared in the above Example 3, an experiment for promoting immunoglobulin production was performed using peripheral blood mononuclear cells (PBMCs).

PBMCs isolated from peripheral blood donated from healthy donors were dispensed in 96-well cell culture plates at $2 \times 10^5$ cells/well, and cultured in an incubator at 37° C. and 5% $CO_2$ environment with a serum-free culture medium containing 10% v/v of immune-tolerized extracellular vesicles (itPG-EVs) containing primal immunoglobulins prepared in Example 3. As control groups, a non-treated group, a group treated with co-cultured extracellular vesicles of hematopoietic stem cells and umbilical cord blood-derived mesenchymal stem cell (HSC/UCB-MSC$^{CO}$-EVs) having innate immunity properties of Example 2, and a group treated with immune-tolerized fetal stem cell-derived extracellular vesicles (itFSC-EVs) cultured under the same culture conditions as in Example 3 with a medium containing only trophoblast-derived extracellular vesicles (itTBC-EVs) having the immune tolerance properties of Example 1, were used. In 2, 4, 8, 12, and 24 hours after incubation, the culture supernatants were collected and the concentrations of IgG3 and IgM, which play a key role in innate immunity among the immunoglobulins present in each culture supernatant, were analyzed by using each ELISA kit.

Figure 4:
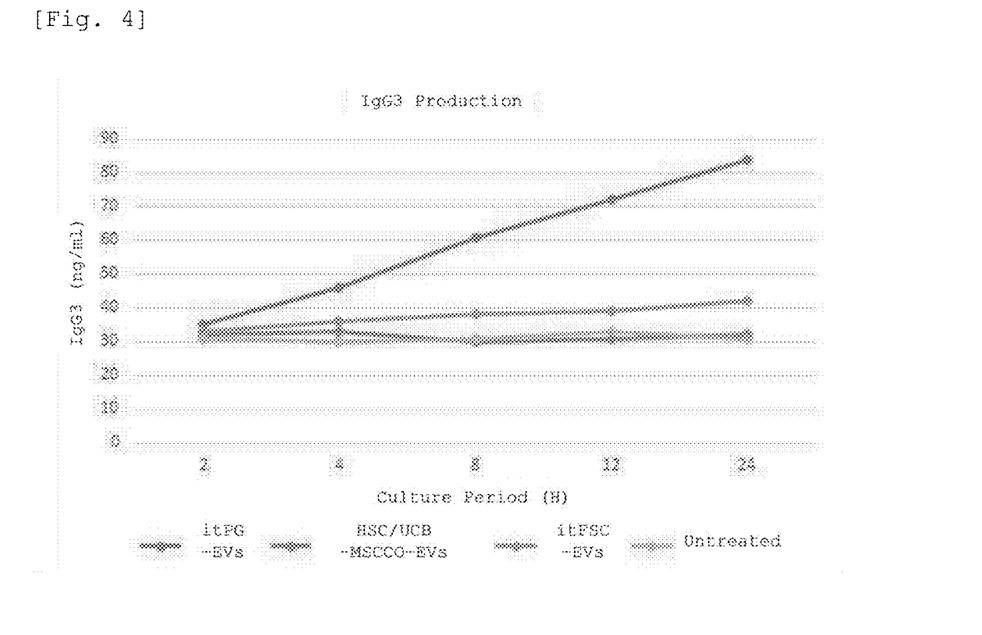
FIG. 4 is a graph showing the effect of promoting the production of IgG3, a natural antibody acting on innate immunity, from peripheral blood mononuclear cells by immune-tolerized extracellular vesicles containing primal immunoglobulins.
Figure 5:
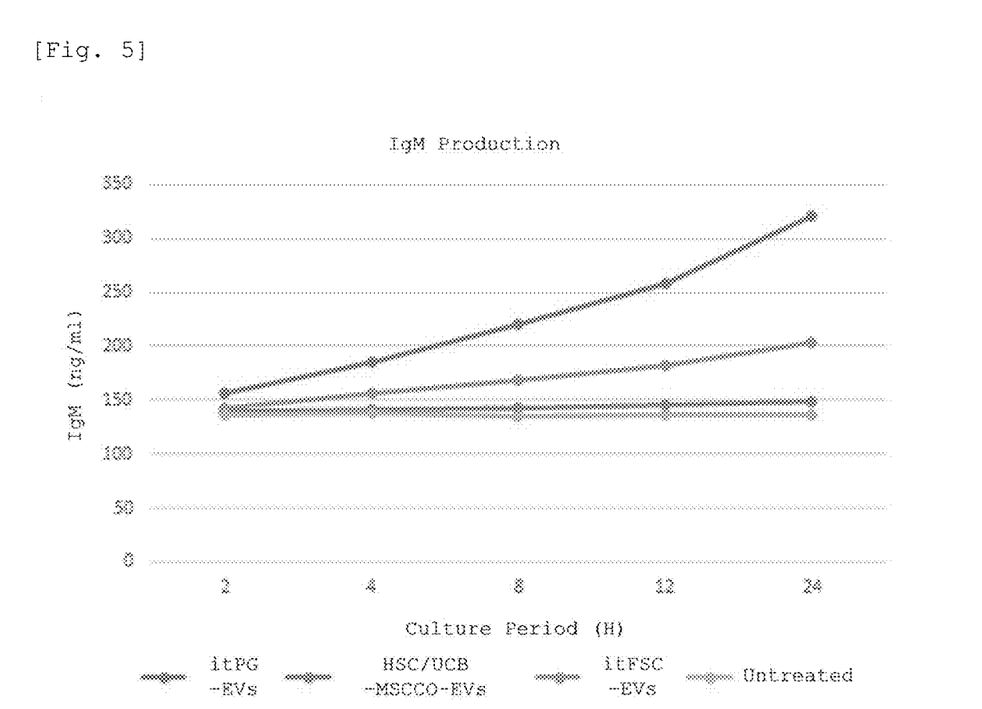
FIG. 5 is a graph showing the effect of promoting the production of IgM, a natural antibody acting on innate immunity, from peripheral blood mononuclear cells by immune-tolerized extracellular vesicles containing primal immunoglobulins.
Figure 6:
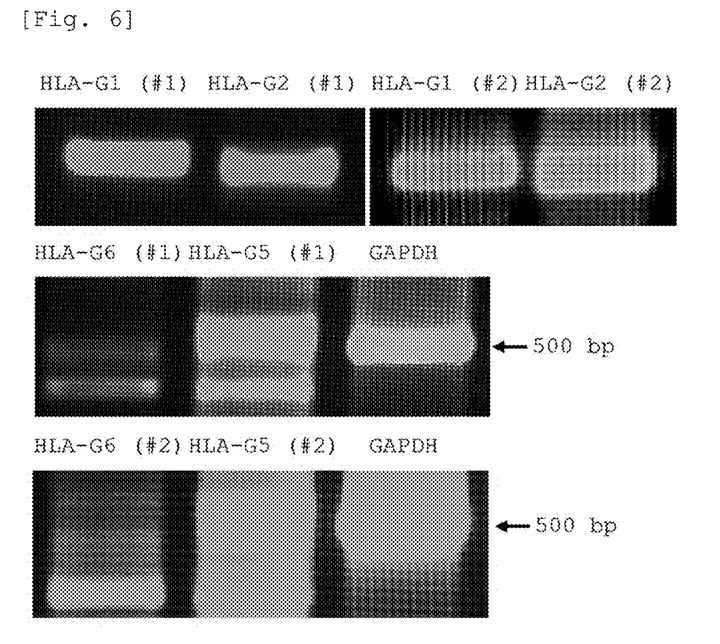
FIG. 6 is a diagram of analyzing various HLA-G mRNA isotypes contained in immune-tolerized extracellular vesicles containing primal immunoglobulins by RT-PCR, and the table at the bottom shows the primer sequences designed for detection of each HLA-G mRNA.
Figure 7:
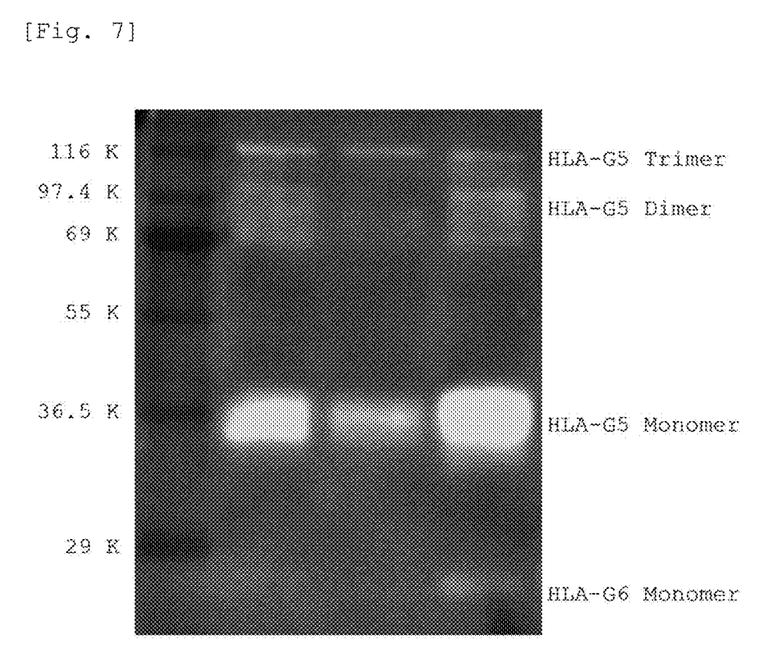
FIG. 7 is a diagram of analyzing various soluble HLA-G proteins contained in immune-tolerized extracellular vesicles containing primal immunoglobulins by Western blot.

As a result, as shown in FIGS. 4 and 5, it could be confirmed that IgG3 and IgM productions are hardly changed or slightly increased for 24 hours in control groups, the non-treated group, the HSC/UCB-MSC$^{CO}$-EVs treated group, and the itFSC-EVs treated group, while the productions of IgG3 and IgM are significantly increased in the group treated with immune-tolerized extracellular vesicles (itPG-EVs) containing primal immunoglobulins prepared in Example 3 of the present invention.

Accordingly, it could be confirmed that the immune-tolerized extracellular vesicles containing primal immunoglobulins of the present invention significantly promote the production of natural antibodies responding immediately to foreign antigens in the innate immune system, thereby providing the efficacy of preventing and treating infectious diseases caused by foreign infectious agents.

Example 5: Analysis of HLA-G mRNA Contained in the Immune-Tolerized Fetal Stem Cells Secreting Primal Immunoglobulins and Analysis of Progesterone and HLA-G Protein Contained in Extracellular Vesicles (itPG-EVs) Secreted Therefrom HLA-G mRNA for inducing immune tolerance expressed in the immune-tolerized fetal stem cells secreting primal immunoglobulins established in the above Example 3 was analyzed by RT-PCR. Total RNA was extracted from immune-tolerized fetal stem cells using TRIzol according to the manufacturer's instructions (Invitrogen by Thermo Fisher Scientific, Waltham, MA, USA). A total of 1 ug of DNase-treated RNA was transcribed into cDNA by using 200 units of Superscript II reverse transcriptase (Invitrogen) and 150 ng of random primers (Invitrogen). Primer sequences for various isotypes of HLA-G mRNA are shown in table 5. All PCR samples were analyzed by electrophoresis on a 2% agarose gel (Amresco, Solon, OH, USA) containing 0.5 ug/ml ethidium bromide (Sigma-Aldrich). As a result, it was confirmed that HLA-G1, G2, G5, and G6 mRNAs are all expressed in the immune-tolerized fetal stem cells secreting primal immunoglobulins established in the above Example 3.

TABLE 5

Primer sequences designed to analyze various HLA-G mRNAs contained in the immune-tolerized extracellular vesicles (itPG-EVs) containing primal immunoglobulins

| Gene | Forward Sequence | Target Region | Reverse Sequence | Target Region | Amplicon Size (bp) |
|---|---|---|---|---|---|
| HLA-G1 | GGCTGAAC AAAGGAGA GCCTA | Exon 3 | TACAGCTG CAAGGACA ACCA | Exon 5 | 436 |
| HLA-G2 | GGGAAGAG GAGACACG GAAC | Exon 2 | TACAGCTG CAAGGACA ACCA | Exon 5 | 438 |
| HLA-G5 | CCTCCAGT GGATGATT GGCT | Exon 3 | CTCCTGCT TTCCCTAA CAGACA | Intron 4 | 588 |
| HLA-G6 | CCACGCAC AGACTGAC AGAA | Exon 2 | GAGGCTCC TGCTTTCC CTAA | Intron 4 | 391 |

In addition, the soluble HLA-G protein inducing immune tolerance contained in the immune-tolerized extracellular vesicles (itPG-EVs) containing primal immunoglobulins prepared in the above Example 3 was analyzed by Western blot. To extract HLA-G protein from the extracellular vesicles, the protein was precipitated by using trichloroacetic acid and then loaded on 10% SDS-PAGE. Then, the protein was extracted from the extracellular vesicles by electrophoresis and transferred to a polyvinylidene difluoride membrane, after which a 5A6G7 primary antibody binding to Intron 4 position of the soluble HLA-G protein was attached, and then HRP-conjugated secondary goat anti-mouse IgG antibody (Abcam) was attached. An expression level of each isotype of HLA-G was detected by using an ECL solution kit (Thermo Fisher Scientific) and a Chemiluminescence imaging system (Alliance Mini HD9, UVITEC, Cambridge, UK). As a result, it was confirmed that soluble HLA-G5, G6 monomer, and HLA-G5 dimers and trimers are present in the immune-tolerized extracellular vesicles (itPG-EVs) containing primal immunoglobulins prepared in the above Example 3.

In addition, the concentration of progesterone that promotes the expression and secretion of HLA-G inducing immune tolerance contained in the immune-tolerized extracellular vesicles (itPG-EVs) containing primal immunoglobulins prepared in the above Example 3 was analyzed by using the Progesterone ELISA Kit (Elabscience). As a result, it was confirmed that itPG-EVs contain 2.25±0.61 ng/ml of progesterone.

From the description above, those skilled in the art, to which the present invention pertains, will understand that the present invention may be practiced in other specific forms without changing the technical scope or essential features thereof. In this regard, it should be understood that the exemplary embodiments described above are illustrative in all aspects, and thus the present invention is not limited thereto. It should be understood that the scope of the present invention includes all the modifications or changed forms derived from the meaning and scope of the patent claims to be described below as well as equivalents thereto, rather than the detailed descriptions above.

The invention claimed is:
1. An extracellular vesicle derived from human fetal stem cells, the extracellular vesicle comprising:
  immunoglobulin M, immunoglobulin A, immunoglobulin D, immunoglobulin G, immunoglobulin G3, and immunoglobulin E,
  wherein the extracellular vesicle further contains HLA-G proteins,
  wherein the extracellular vesicles are prepared by:
  (a) obtaining human trophoblast-derived extracellular vesicles from the human trophoblast expressing and secreting HLA-G;
  (b) obtaining extracellular vesicles from the hypoxic co-culture of human hematopoietic stem cells and human umbilical cord blood-derived mesenchymal stem cells;
  (c) inoculating the human fetal stem cells derived from amniotic fluid obtained during amniocentesis around 15 weeks of pregnancy into a matrix gel comprising hyaluronic acid, and subculturing in a serum-free medium containing the trophoblast-derived extracellular vesicles of step (a) and the extracellular vesicles of step (b);
  (d) inoculating the subcultured fetal stem cells of step (c) into a culture plate and culturing in a serum-free medium, so as to obtain a culture supernatant; and
  (e) filtering the culture supernatant and isolating the extracellular vesicles derived from human fetal stem cells,
  wherein the trophoblast-derived extracellular vesicles of step (a) are prepared by:
  (a-1) obtaining extracellular vesicles from the co-culture of human amniotic membrane-derived mesenchymal stem cells and amniotic fluid-derived mesenchymal stem cells;
  (a-2) inoculating human trophoblast cells into a matrix gel containing hyaluronic acid in the presence of the extracellular vesicles of step (a-1); and
  (a-3) culturing the trophoblast cells of step (a-2),
  wherein the extracellular vesicles obtained from the hypoxic co-culture of human hematopoietic stem cells and umbilical cord blood-derived mesenchymal stem cells of step (b) are prepared by:
  (b-1) inoculating human hematopoietic stem cells and umbilical cord blood-derived mesenchymal stem cells in upper and lower wells of a co-culture plate, respectively;
  (b-2) co-culturing in a serum-free medium under 1 to 5% $O_2$ to obtain a culture supernatant; and
  (b-3) filtering the culture supernatant and isolating the extracellular vesicles.

2. The extracellular vesicle of claim 1, further comprising:
estrogen,
octamer-binding protein 1 (OCT-1),
octamer-binding protein 2 (OCT-2),
nuclear factor ikappa-light-chain-enhancer of activated B cells (NF-KB),
immunoglobulin lambda-like polypeptide-1 (IGLL1), and
cleavage stimulation factor (CstF).

3. The extracellular vesicle of claim 1, further comprising:
complement subcomponent 1q (C1q),
complement subcomponent 1r (C1r),
complement subcomponent 1s (C1s),
complement component 2 (C2),
complement component 3 (C3),
complement component 3a (C3a),
complement component 4a (C4a),
complement component 5/5a (C5/C5a),
complement component 7 (C7),
complement component 8 (C8) beta chain,
complement component 9 (C9),
complement factor B,
complement factor mannose-binding lectin-associated serine protease-3 (MASP-3),
interferon-induced transmembrane protein 3 (IFITM3),
lymphocyte antigen 6 family member E (LY6E), and
transient receptor potential cation channel, mucolipin subfamily, member 2 (TRPML2).

4. The extracellular vesicle of claim 1, further comprising:
progesterone,
human leukocyte antigen G1 (HLA-G1),
human leukocyte antigen G2 (HLA-G2),
human leukocyte antigen G5 (HLA-G5), and
human leukocyte antigen G6 (HLA-G6).

5. A pharmaceutical composition for of treating infectious diseases caused by a foreign infectious agent, comprising an extracellular vesicle of any one of claims 1 to 4.

6. A composition for enhancing innate immunity, comprising an extracellular vesicle of any one of claims 1 to 4.

* * * * *